United States Patent [19]

Grundei

[11] Patent Number: 4,676,795
[45] Date of Patent: Jun. 30, 1987

[54] PROSTHESIS AS REPLACEMENT FOR AN AMPUTATED BREAST

[75] Inventor: Hans Grundei, Lübeck, Fed. Rep. of Germany

[73] Assignee: S+G Implants GmbH, Lubeck, Fed. Rep. of Germany

[21] Appl. No.: 785,481

[22] Filed: Oct. 8, 1985

[30] Foreign Application Priority Data

Oct. 13, 1984 [DE]  Fed. Rep. of Germany ....... 3437591
Nov. 9, 1984 [DE]  Fed. Rep. of Germany ....... 3440960

[51] Int. Cl.⁴ ............................................. A61F 2/12
[52] U.S. Cl. ................................................... 623/8
[58] Field of Search ................... 623/7, 8; 5/450, 451

[56] References Cited

U.S. PATENT DOCUMENTS

| | | | |
|---|---|---|---|
| 2,636,182 | 4/1953 | Freedman | 623/7 |
| 3,574,873 | 4/1971 | Weinstein | 5/450 |
| 3,911,503 | 10/1975 | Hankin | 623/7 |

Primary Examiner—Richard J. Apley
Assistant Examiner—James Prizant
Attorney, Agent, or Firm—Balogh, Osann, Kramer, Dvorak, Genova & Traub

[57] ABSTRACT

The prosthesis as replacement for an amputated breast consists of a shell modelled to the shape of the breast made of elastic material, in which, apart from a filled, slowly flowing mass, at least one elastically deformable, porous molding is provided. The slowly flowing mass advantageously consists of a gel-like or partially vulcanized silicone rubber, due to which the porous molding is substantially fixed in its position in the shell.

7 Claims, 4 Drawing Figures

PROSTHESIS AS REPLACEMENT FOR AN AMPUTATED BREAST

BACKGROUND OF THE INVENTION

1. Field of the Invention

The invention relates to a prosthesis as replacement for an amputated breast, consisting of a shell modelled to the shape of the breast, made of elastic material with a filling of a slowly flowing mass.

2. Description of the Prior Art

Known prostheses of the previously mentioned type which are generally supported by a brassiere and are matched to the thorax have the advantage that the prosthesis can move swingingly like a normal breast with body movements due to the slowly flowing mass, in particular gel-like silicone rubber, and the elastic shell. However, the shell filling makes the prosthesis relatively heavy and it is therefore felt to be uncomfortable by the women.

OBJECTS AND SUMMARY OF THE INVENTION

The object of the invention consists in improving the known prostheses such that their weight is substantially reduced, but that the swinging movements of the prosthesis as with a natural breast continue to be ensured.

This object is achieved according to the invention by at least one elastically deformable, porous molding being provided in the shell of such known prosthesis.

By using the porous molding, which advantageously either has an open-cell, sponge-like structure or consists of a grid-like filament skeleton or filament web, the weight of the prosthesis is substantially reduced as the molding has a relatively low weight due to its porous structure. Due to the structure of the molding, when there are body movements the slowly flowing mass, which consists in particular of gelled or partially vulcanized silicone rubber, can move in and out of the pores or cells of the molding to a partial depth and the molding can deform elastically due to the movement of the gel-like mass so that the prosthesis behaves like a natural breast.

The swinging movement can be promoted by a cavity being provided between the gel-like mass and the molding, promoting the free movement of the mass.

The porous molding can also consist of two or more elements or of several parts, e.g. be laminated or composite. The only partially vulcanized or gelled mass, in particular of silicone rubber, makes the mass penetrate into the pores on the periphery of the molding and, depending the formulation of the composition, gel or vulcanize to a greater or lesser extent from the original liquid state, so that this mass is practically jointed to the molding and substantially fixes this molding in its position fitted in the shell.

In the case of a particularly advantageous embodiment, the molding is arranged in the region of the wall of the shell facing the thorax, so that the other part can remain movable and can swing upon deformation of the molding.

BRIEF DESCRIPTION OF THE DRAWINGS

The invention is explained, by way of example, with reference to two exemplary embodiments in the drawings, in which.

DETAILED DESCRIPTION OF THE PREFERRED EMBODIMENTS

Figure 1:
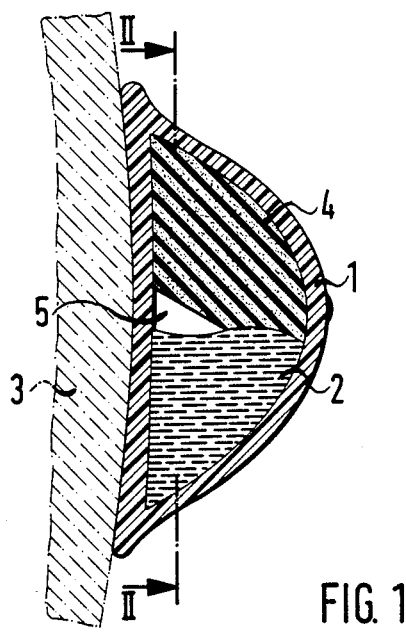
FIG. 1 shows a vertical section through a breast prosthesis according to a first example.
Figure 2:
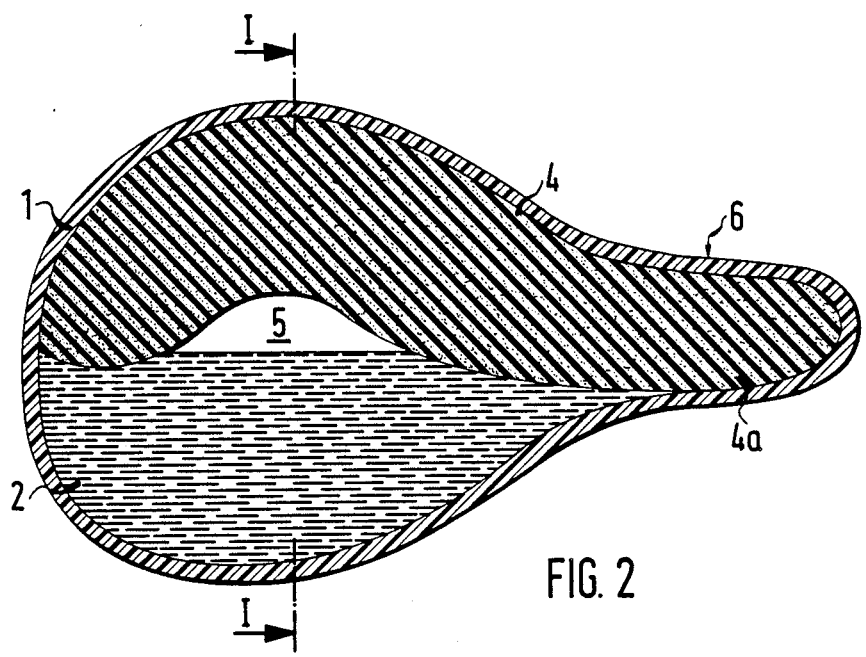
FIG. 2 shows a section along the line II—II of FIG. 1.

According to FIGS. 1 and 2, the prosthesis consists of a closed shell 1, modelled on the natural breast, which is made for example in a known way of elastic, fully vulcanized silicone rubber or of an identically acting, elastic material. This shell 1 is partially filled with a slowly flowing, gel-like mass, in particular with an only partially vulcanized or gelled, and therefore flowing, gel-like silicone rubber 2, this slowly flowing filling part 2 taking up the bottom part of the shell interior when the prosthesis is worn on the body 3. The remaining upper interior of the shell 1 is taken up by an elastically deformable molding 4 of open-cell or continuously open-pore structure, which corresponds to that of a natural or artificial sponge and consists of a suitable plastic or rubber.

This molding 4 advantageously has the structure of a grid-like filament skeleton or of a filament web of rubber, silicone rubber or a plastic, such as for example PVC, polyamide, polyurethane or the like.

Due to the open-cell molding 4, the weight of the prosthesis can be kept extremely low, so that the prosthesis is no longer felt as troublesome by the women and, in particular, with body movements the movement of the flowly flowing mas 2 is not hindered as the mass can elastically deform the molding 4 with movements of the woman's body and penetrate and flow back into and out of the molding 4 at least to a partial depth, so that the prosthesis behaves like a natual breast upon movement of the woman. This movement of the filling mass 2 can be promoted by a cavity 5 being provided between the gel-like mass 2 and the molding 4, into which cavity the mass 2 can flow in and then flow out again.

It is known to provide a prosthesis modelled on the breast with a lateral, lug-like extension which is generally forcibly brought into contact with the side of the thorax by a brassiere, for example to cover the axillary lymph gland region.

Figure 4:
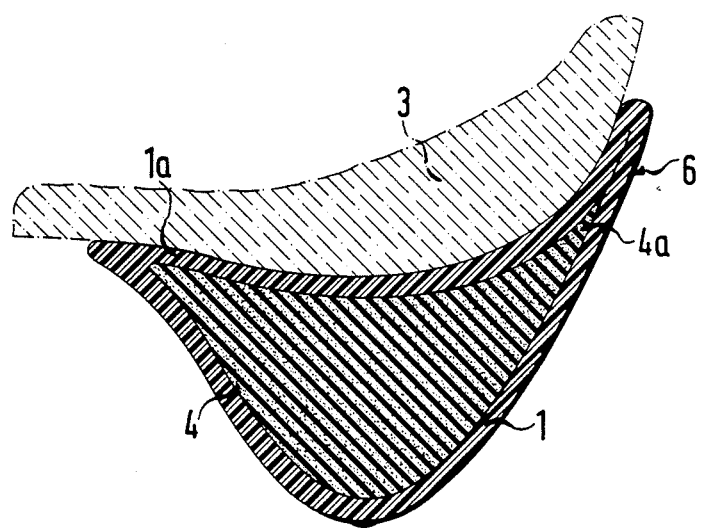
FIG. 4 shows a horizontal section through the upper region of the prosthesis according to FIG. 1.

In contrast, the approach according to the invention is for the shell 1 of the prosthesis to form on one side the lap-like extension 6 which is filled out by an extension 4a of the molding 4. According to the invention, the molding 4 with the extension 4a and the shaped shell 1 bring the prosthesis into a position in which the prosthesis is an arcuately curved, dimensionally stable, elastic structure, the surface of which in contact with the thorax 3 is substantially concave. Thus, a matching of the prosthesis to the shape of the thorax is achieved from the outset and it is no longer necessary for a brassiere to enforce this fitting shape. The associated embodiment is shown in FIG. 4.

Figure 3:
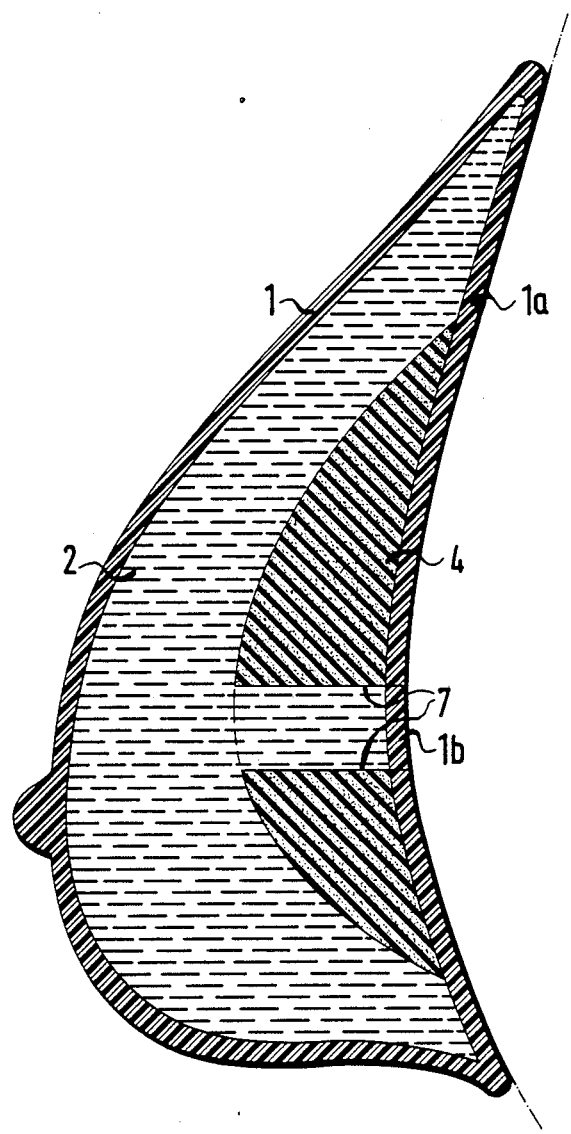
FIG. 3 shows a vertical section through a breast prosthesis, according to a further exemplary embodiment.

According to the particularly advantageous example of FIG. 3, in which the same reference symbols as FIGS. 1 and 2 are used for the same parts, an elastically deformable, porous molding 4, or several moldings, are fitted into the elastic shell. The molding 4, which may also be made up of several parts or layers, is advantageously located in the region of the shell wall 1a facing the thorax, so that the movable gel-type mass 2 takes up the outer interior of the shell 1, the swinging movement of the breast when the wearer walks simulating particularly well the swinging movement of a natural breast.

In this case, after filling in the shell 1, the flowing mass 2 is intended, depending on the composition, to penetrate to a greater or lesser extent into the pores on the periphery of the molding 4 and assume a gel-like or partially vulcanized state, so that this makes the mass 2 fix the molding 4 substantially in its position in the shell.

In this case, the molding 4 is provided with a channel-shaped passage 7 for filling of the slowly flowing mass 2, and the shell wall 1a must have a passage 1b aligning with the channel, so that filling of the gel-like mass 2 into the shell 1 can take place through these passages. The shell passage 1b is subsequently closed again.

Instead of a gel-like mass of silicone rubber, other masses, such as oils, pastes and the like, may also be used as filling material. Thus, the term "slowly flowing mass" is not necessarily to be understood as a liquid mass. For example, gel-like masses or partially cold-vulcanized masses are in this sense "slowly flowing" if, although they allow themselves to be flowingly elastically deformed under the effect of a force, after the force has been removed they substantially revert to their original shape.

Whilst the invention and many of its attendant advantages will be understood from the foregoing, it will be apparent that various changes may be made in the form, construction and arrangement of the parts, or in the nature of the materials used without departing from the spirit and scope of the invention or sacrificing all of its material advantages, the forms hereinbefore described merely being preferred embodiments thereof.

The embodiments of the invention in which an exclusive property or privilege is claimed are defined as follows:

1. A breast prosthesis, consisting of a closed envelope of elastic material imitating the natural breast form, containing a molded body of elastically deformable, porous synthetic material occupying a substantial portion of the internal volume defined by said envelope, and a quantity of flowing, only partly vulcanized silicone rubber in direct fludic communication with said body of porous synthetic material, so that the weight of the prosthesis is reduced for a given displacement of volume over the eight which a similarly shaped prosthesis envelope containing only fluid would have.

2. A breast prosthesis according to claim 1, wherein the molding consists of a porous, grid-like filament skeleton.

3. Breast prosthesis according to claim 1, wherein the elastically deformed molding body is arranged in an outer portion of the envelope.

4. Breast prosthesis according to claim 1, wherein the elastically deformable molding body is arranged in a portion of the envelope facing the breast.

5. Breast prosthesis according to claim 1, wherein a free space is provided between the molding body and the only partly vulcanized silicone rubber.

6. Breast prosthesis according to claim 1, wherein the envelope is provided to the arm side with a flap-type continuation, the envelope with its contents and with the continuation is a form-stable, arcuately curved, elastically deformable structure, the surface of the envelope lying on the thorax being essentially concave.

7. Breast prosthesis according to claim 4, wherein the molding body has, in its middle portion, a free passage which aligns with a closable passage of the envelope wall.

* * * * *